(12) United States Patent
Thomson et al.

(10) Patent No.: US 6,556,651 B1
(45) Date of Patent: Apr. 29, 2003

(54) ARRAY OF MINIATURE RADIATION SOURCES

(75) Inventors: Euan Thomson, Harvard, MA (US); Mark Dinsmore, Sudbury, MA (US)

(73) Assignee: Photoelectron Corporation, North Billerica, MA (US)

( * ) Notice: Subject to any disclaimer, the term of this patent is extended or adjusted under 35 U.S.C. 154(b) by 0 days.

(21) Appl. No.: 10/133,103

(22) Filed: Apr. 26, 2002

Related U.S. Application Data

(60) Provisional application No. 60/351,805, filed on Jan. 25, 2002.

(51) Int. Cl.[7] .................................................. A61N 5/10
(52) U.S. Cl. .......................... 378/65; 378/134; 378/136
(58) Field of Search ........................... 378/65, 134, 136

(56) References Cited

U.S. PATENT DOCUMENTS 5,729,583 A * 3/1998 Tang et al. .................... 378/65

FOREIGN PATENT DOCUMENTS

WO          WO 02/41947 A2      5/2002

* cited by examiner

*Primary Examiner*—Craig E. Church
(74) *Attorney, Agent, or Firm*—McDermott, Will & Emery

(57) ABSTRACT

A system for delivering therapeutic radiation, such as x-rays, to a treatment region includes a plurality of individually controllable therapeutic radiation sources. The therapeutic radiation sources are selectively and moveably disposed along one or more axes, or upon a two-dimensional surface, or within a three-dimensional volume, so as to form a one-dimensional or a multi-dimensional array. Each therapeutic radiation source includes an electron source for emitting electrons, and an associated target element adapted to emit therapeutic radiation in response to incident electrons. In one embodiment, each therapeutic radiation source is coupled to a distal end of an associated optical delivery structure, which is adapted to direct a beam of optical radiation to impinge upon a surface of the electron source so as to cause emission of electrons therefrom.

40 Claims, 6 Drawing Sheets

ARRAY OF MINIATURE RADIATION SOURCES

CROSS-REFERENCE TO RELATED APPLICATIONS

This application claims benefit of U.S. Provisional Application Serial No. 60/351,805, entitled "Array of Miniature Radiation Sources" and filed on Jan. 25, 2002.

STATEMENT REGARDING FEDERALLY SPONSORED RESEARCH

Not Applicable

REFERENCE TO MICROFICHE APPENDIX

Not Applicable

BACKGROUND

In the field of medicine, radiation may be used for diagnostic, therapeutic and palliative purposes. Therapeutic use of radiation such as x-rays and γ-rays typically involves using these rays to eradicate malignant cells. Conventional radiation treatment systems used for medical treatment, such as linear accelerators that produce high-energy x-rays, utilize a remote radiation source external to the targeted tissue. A beam of radiation is directed at the target area, for example a malignant tumor inside the body of a patient. The x-rays penetrate the patient's body tissue and deliver radiation to the cancer cells, usually seated deep inside the body. This type of treatment is referred to as teletherapy because the radiation source is located at some distance from the target. This treatment suffers from the disadvantage that tissue disposed between the radiation source and the target is exposed to radiation. To reach the cancer cells, the x-rays from an external radiation source must usually penetrate through normal surrounding tissues. Non-cancerous tissues and organs are thus also damaged by the penetrating x-ray radiation.

Brachytherapy, on the other hand, is a form of treatment in which the source of radiation is located close to, or in some cases within, the area receiving treatment. Brachytherapy, a word derived from the ancient Greek word for close ("brachy"), offers a significant advantage over teletherapy, because the radiation is applied primarily to treat only a predefined tissue volume, without significantly affecting the tissue adjacent to the treated volume. The term brachytherapy is commonly used to describe the use of "seeds," i.e. encapsulated radioactive isotopes, which can be placed directly within or adjacent to the target tissue being treated. Handling and disposal of such radioisotopes, however, may impose considerable hazards to both the handling personnel and the environment. Also, introduction of the radioisotopes requires invasive procedures which have potential side-effects, such as the possibility of infection. Moreover, there is no ability to provide selective control of time dosage or radiation intensity.

The term "x-ray brachytherapy" is defined for purposes of this application as x-ray radiation treatment in which the x-ray source is located close to or within the area receiving treatment. An x-ray brachytherapy system, which utilizes a miniaturized low power radiation source that can be inserted into, and activated from within, a patient's body, is disclosed in U.S. Pat. No. 5,153,900 issued to Nomikos et al., U.S. Pat. No. 5,369,679 to Sliski et al., U.S. Pat. No. 5,422,926 to Smith et al., and U.S. Pat. No. 5,428,658 to Oettinger et al., all owned by the assignee of the present application, all of which are hereby incorporated by reference.

The x-ray brachytherapy systems disclosed in the above-referenced patents include miniaturized, insertable x-ray probes that are capable of controllably producing and delivering low power x-ray radiation, while positioned within or in proximity to a predetermined region to be irradiated. In this way, x-ray radiation need not pass through the patient's skin, bone, or other tissue prior to reaching the target tissue. The probe may be fully or partially implanted into, or surface-mounted onto a desired area within a treatment region of a patient. X-rays are emitted from a nominal, or effective "point" source located within or adjacent to the desired region to be irradiated, so that substantially only the desired region is irradiated, while irradiation of other regions are minimized. X-ray brachytherapy offers the advantages of brachytherapy, while avoiding the use and handling of radioisotopes. Also, x-ray brachytherapy allows the operator to control over time the dosage of the delivered x-ray radiation.

X-ray brachytherapy treatment generally involves positioning the insertable probe into or adjacent to the tumor or the site where the tumor or a portion of the tumor was removed to treat the tissue adjacent the site with a local boost of radiation. X-ray probes of the type generally disclosed in U.S. Pat. No. 5,153,900 include a capsule, and a hollow, tubular probe or catheter extending from the capsule along an axis, and having an x-ray emitting target element at its distal end. The probe may enclose an electron source, such as a thermionic cathode. In one form of a thermionic cathode, a filament is resistively heated with a current. This in turn heats the cathode so that electrons are generated by thermionic emission.

In another form of an x-ray brachytherapy device, as disclosed in U.S. Pat. No. 5,428,658, an x-ray probe may include a flexible probe, such as a flexible fiber optic cable enclosed within a metallic sheath. The x-ray probe may also include a substantially rigid, evacuated capsule that is coupled to a distal end of the flexible probe. The capsule encloses an optically activated electron source, such as a photocathode, and an x-ray emissive target element. In a photocathode configuration, a photoemissive substance is irradiated by a LED or a laser source, causing the generation of free electrons. Typically, a flexible fiber optic cable couples light from a laser source or a.LED to the photocathode.

U.S. patent application Ser. No. 09/884,561 (hereinafter the "'561 application") (commonly owned by the assignee of the present invention and incorporated herein by reference), entitled "Optically Driven Therapeutic Radiation Source," discloses an optically driven (for example, laser driven) therapeutic radiation source that uses a reduced-power, increased efficiency electron source to generate electrons with minimal heat loss. The '561 application discloses the use of laser energy to heat an electron emissive surface of a thermionic emitter, instead of using an electric current to ohmically heat an electron emissive surface of a thermionic emitter. With the optically driven thermionic emitter, electrons can be produced in a quantity sufficient to produce the electron current necessary for generating therapeutic radiation at the target, while significantly reducing the requisite power requirements. U.S. patent application Ser. No. 10/005,290 hereby discloses a therapeutic radiation source having an in situ radiation detector, which permits real-time monitoring of the therapeutic radiation that is being generated and delivered.

Even though the above-discussed miniature radiation sources can generate x-rays local to the target tissue, it is difficult to provide a uniform, or other desired, dose of radiation to an irregularly shaped target tissue, using these radiation sources. These miniature radiation sources generally act as point sources of therapeutic radiation. The intensity of the radiation from a point source decreases uniformly with approximately the square of the distance (R) from the source (i.e., $1/R^2$). Since body cavities, or the beds of resected tumors, are not generally spherically symmetrical, a point source within a body cavity or central to the resected tumor bed will not deliver a uniform dose of radiation to the tissue lining of the cavity or bed. Likewise, a point source at the center of a non-spherical tumor will not deliver radiation with an isodose contour matching the peripheral surface of the tumor.

The treatment regions within a patient's anatomical structure are usually not adapted for uniform or spherically isotropic patterns of irradiation, because the organs or body cavities being treated during radiation therapy usually have arbitrary and irregular shapes and geometries. The areas of a patient's body requiring treatment may be characterized by twists and bends. In some cases, the geometry of the target region may not be fixed, as in the bladder for example, which has a flexible inner wall without a well-defined shape. Also, some treatment procedures may require delivery of localized radiation to portions of the human body that are not easily accessible. Cancerous tumors are usually shaped irregularly, and are distributed randomly across a given anatomical region. A single point source of therapeutic radiation, even when inserted into and activated within a patient's body, cannot deliver a uniform dose of radiation to a desired area within an irregularly shaped body cavity or organ, nor can it deliver more complex radiation dose patterns that may be desirable or required for some cases. Similarly, a single point source at the center of a non-spherical tumor will not deliver radiation with an isodose contour matching the peripheral surface of the tumor, as discussed earlier.

For the foregoing reasons, there is a need for devices and methods which overcome the above-discussed limitations of brachytherapy, by enabling a more versatile, efficient, and versatile delivery of localized therapeutic radiation, while still preserving the advantages of brachytherapy. In particular, an arrangement in which a plurality of point-like sources of therapeutic radiation are positioned over the desired treatment region as a one- or a multi-dimensional array would significantly increase user control over the intensity and duration of the therapeutic radiation being delivered, and would enable the user to achieve complex radiation profiles.

SUMMARY

The present invention provides a system for delivering therapeutic radiation, in which a plurality of therapeutic radiation sources are arranged over a desired treatment region as a one- or a multi-dimensional array. In one embodiment, the therapeutic radiation consists of x-rays, although the scope of this invention is not limited to x-ray sources. In a preferred embodiment of the invention, the plurality of therapeutic radiation sources are selectively and moveably disposed on a two-dimensional (2-D) surface, and arranged into a two-dimensional array. Alternatively, the plurality of therapeutic radiation sources may be selectively and moveably disposed along an axis so as to form a one-dimensional (1-D) array. Alternatively, the plurality of therapeutic radiation sources may be selectively and moveably disposed within a three-dimensional (3-D) volume and arranged into a three-dimensional array. The therapeutic radiation sources may be disposed on two-dimensional surfaces having any desired configuration, including rigid, flexible, planar, concave, convex, spherical, or cylindrical surfaces. The axes defining the arrays may also have any desired shape or configuration, including straight, curvilinear, rigid, or flexible axes. The therapeutic radiation sources may be regularly or variably spaced along the one- or multi-dimensional arrays.

Each therapeutic radiation source includes an electron source, such as a cathode. The cathode may be a thermionic cathode, a cold cathode or a photocathode. The thermionic cathode may be a resistively heated thermionic cathode, or a laser-heated thermionic cathode. The electron source emits electrons to generate an electron beam along a beam path. A target element is positioned in the beam path. The target element includes at least one radiation emissive material for emitting radiation, for example x-rays, in response to incident accelerated electrons from the electron beam.

An accelerating voltage is provided between each electron source and each associated target element, so that an accelerating electric field is established which acts to accelerate electrons emitted from the electron source toward the associated target element. The therapeutic radiation sources are individually controllable, i.e. the intensity and duration of the emitted therapeutic radiation can be individually controlled for each therapeutic radiation source.

In an embodiment of the invention, the system for delivering therapeutic radiation further includes a plurality of optical delivery structures, each optical delivery structure being associated with a corresponding one of the plurality of therapeutic radiation sources. In a preferred embodiment, the optical delivery structure is a fiber optic cable. The system further includes one or more light sources which generate a beam of light directed to the proximal end of each fiber optic cable. Preferably, the one or more light sources are laser sources that generate a laser beam. In this embodiment, the electron source in each therapeutic radiation source emits electrons in response to light transmitted to the distal end of the associated fiber optic cable. The electron source may be an optically heated thermionic cathode, or a photocathode. The optically heated thermionic cathode has an electron emissive surface adapted to emit electrons when heated to a sufficient temperature by a beam of optical radiation, such as laser light. The photocathode has a photoemissive surface, and is responsive to optical radiation incident thereon to emit electrons from the photoemissive surface.

DETAILED DESCRIPTION

In overview, the present invention provides a system for delivering therapeutic radiation, in which a plurality of individually controllable, miniaturized therapeutic radiation sources are used, instead of a single, point-like source of therapeutic radiation. The plurality of therapeutic radiation sources are strung together so as to form an array. In a preferred embodiment, each miniaturized radiation source is an electron-beam activated x-ray source, although sources of other types of therapeutic radiation are also within the scope of this invention. In a preferred embodiment, each x-ray source operates at relatively low voltages, i.e. in the range of approximately 10 kV to 90 kV, and using relatively small electron beam currents, i.e. in the range of approximately 1 nA to 1 mA.

Figure 1:
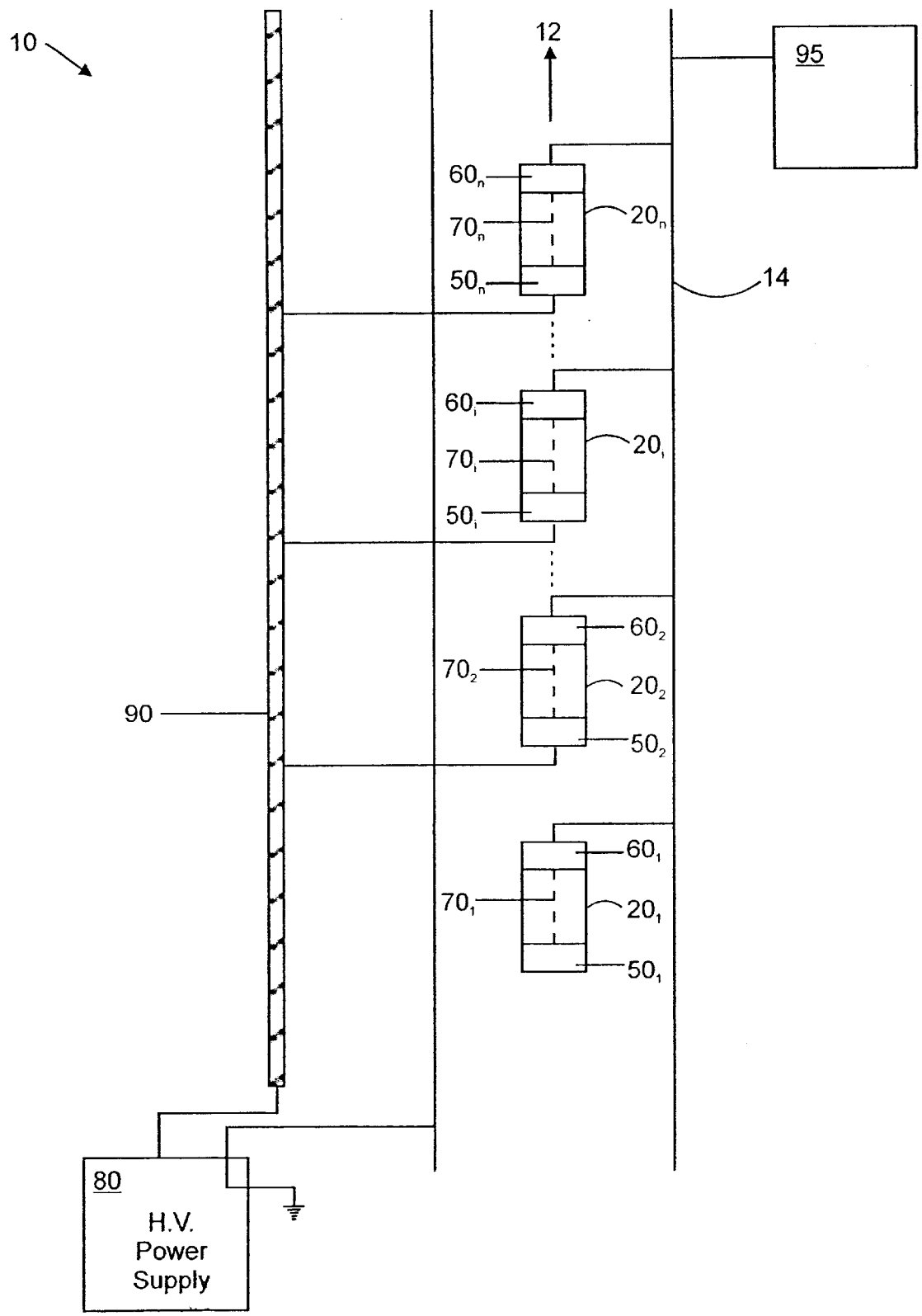
FIG. 1 illustrates a system for delivering therapeutic radiation, in which a plurality of miniature x-ray sources are arranged along an axis in a one-dimensional array.

FIG. 1 provides an illustration of one embodiment of a system 10 for delivering therapeutic radiation, constructed in accordance with the present invention. The system includes a plurality of therapeutic radiation sources $20_1$, $20_2, \ldots, 20_i, \ldots, 20_n$, disposed along an axis 12 so as to form a one-dimensional array. In the illustrated embodiment, each therapeutic radiation source $20_i$ is a miniaturized, point-like source of x-ray radiation, although other sources of therapeutic radiation are also within the scope of this invention.

Each x-ray source $20_i$ comprises an electron source $50_i$, and an associated target element $60_i$. Preferably, the electron source $50_i$ is a cathode. The cathode $50_i$ may be a thermionic cathode. In particular, the cathode $50_i$ may be a resistively heated thermionic cathode, or a laser-heated thermionic cathode which emits electrons when heated to a sufficient temperature. Alternatively, the cathode $50_i$ may be a photocathode, which emits electrons by the photoelectric effect in response to an incident light beam. Alternatively, the cathode $50_i$ may be a cold cathode. A target element $60_i$, associated with the electron source $50_i$, is positioned in the electron beam path. The target element $60_i$ includes at least one x-ray emissive material for emitting x-rays, in response to incident accelerated electrons from the electron beam.

The system 10 includes means for providing an accelerating voltage between each electron source $50_i$ and each associated target element $60_i$, so that an accelerating electric field is established which acts to accelerate electrons emitted from the electron source $50_i$ toward the target element $60_i$. In the illustrated embodiment, the accelerating voltage is provided by a high voltage power supply 80. The high voltage power supply 80 establishes an accelerating electric field between the electron source $50_i$ and the target element $60_i$ in each point-like x-ray source $20_i$, so that electrons emitted from the electron source $50_i$ are accelerated toward the target element $60_i$, and an electron beam is generated along a beam path.

The high voltage power supply 80 preferably satisfies three criteria: 1) small in size; 2) high efficiency, so as to enable the use of battery power; and 3) independently variable x-ray tube voltage and current, so as to enable the unit to be programmed for desired applications. Preferably, the power supply 80 is a programmable power supply, and includes selectively operable control means for selectively controlling the amplitude of the output voltage and the amplitude of the beam generator current. A high-frequency, switch-mode power converter can be used to meet these requirements. The most appropriate topology for generating low power and high voltage is a resonant voltage converter working in conjunction with a high voltage, Cockroft-Walton-type multiplier. Low-power dissipation, switch-mode power-supply controller-integrated circuits (IC) are available for controlling such topologies with few ancillary components. A more detailed description of the power supply 80 is provided in U.S. Pat. Nos. 5,153,900 and 5,428,658.

In the illustrated embodiment, a single high voltage conductive cable 90 provides a connection to each electron source $50_i$ from the high voltage power supply 80. The single high voltage conductive cable 90 is tapped at different locations along the 1-D array, so as to connect the cathode $50_i$ in each x-ray source $20_i$ to the high voltage power supply 80. In this embodiment, the plurality of n x-ray sources are enclosed in a small-diameter, flexible metallic outer catheter or tube 14. The metallic tube is preferably flexible, so as to permit the enclosed array of x-ray sources to navigate through the curves and bends of body passageways. The metallic tube is preferably set at ground potential, in order to reduce the shock hazard of the device. In an exemplary embodiment, the flexible metallic tube 14 may have a diameter of about 1.4 mm, although other sizes may be used. The individual x-ray sources, i.e. the elements of the one-dimensional array, may be uniformly spaced along the axis 12, or may be variably spaced along the axis 12. Markers may be positioned on or within the tube at desired intervals or locations, so as to provide a visual indication of the positions of each x-ray source $20_i$.

The outer flexible tube 14 couples a ground return from each target element $60_i$ to the high voltage power supply 80, thereby establishing a high voltage field between each cathode $50_i$ and each associated target element $60_i$. An insulator (not shown) is provided between the high voltage conductive cable 90 and the grounded flexible tube 14. The flexible tube 14, along with each target element $60_i$, can be coated with a biocompatible outer layer, such as titanium nitride on a sublayer of nickel. For additional biocompatibility, a sheath of, for example, polyurethane can be fitted over the tube 14.

The axis 12, and consequently the one-dimensional array of miniature x-ray sources $20_i$, can have any desired configuration, tailored to a desired radiation dose pattern. For example, the axis 12 may be a substantially straight axis, or a substantially curvilinear axis. The axis 12 may be substantially rigid, or substantially flexible.

The intensity of the x-rays emitted from each x-ray source $20_i$ may be controlled by adjusting 1) the magnitude of the accelerating voltage; and 2) the intensity of the electron beam current. In a preferred embodiment of the invention, the magnitude of the acceleration voltage, as well as the intensity of the electron beam current, are independently controllable for at least two or more of the plurality of x-ray sources $20_i$. In a preferred embodiment, each x-ray source $20_i$ is individually controllable. Increasing the electron beam current results in a directly proportional increase in x-ray emission at all energies. On the other hand, a change in the acceleration voltage results in a total x-ray output variation that is approximately equal to the square of the voltage, with a corresponding shift in the peak x-ray photon energy.

Preferably, the position of each x-ray source $20_i$ is also individually controllable, i.e. each x-ray source $20_i$ is independently moveable within the tube 14. A mechanical assembly 95, illustrated schematically in FIG. 1, can be used to move and manipulate each source $20_i$ within the tube 14. The mechanical assembly 95 may be used to insert each source $20_i$ into the tube 14, and to withdraw each source $20_i$ from the tube. The mechanical assembly 95 may also be used to guide and navigate the tube 14 within a body passageway, such as a blood vessel.

Figure 2A:
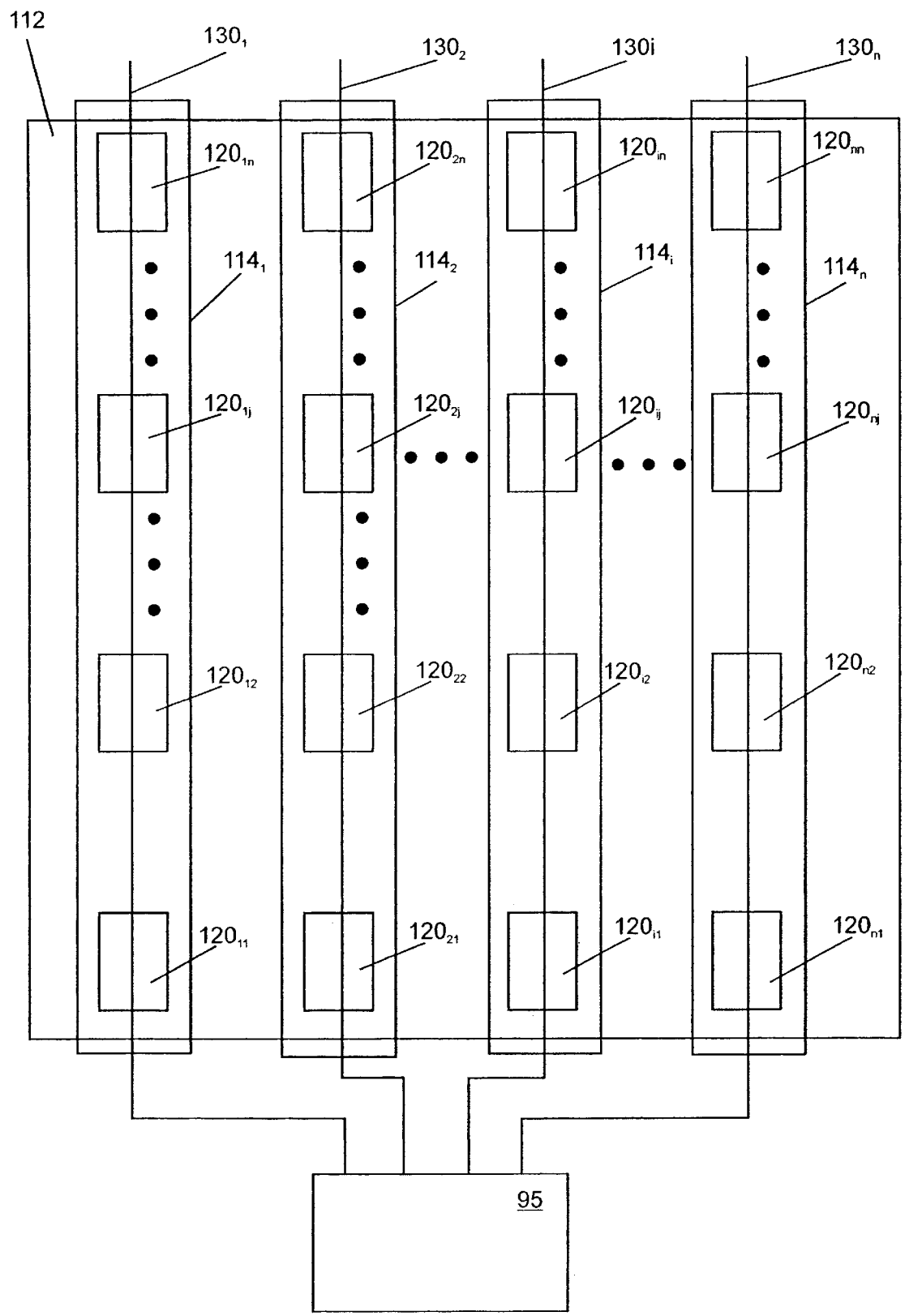
FIGS. 2(*a*) and 2(*b*) illustrates a system for delivering therapeutic radiation, constructed in accordance with the present invention, in which a plurality of x-ray sources are disposed on a two-dimensional surface, and arranged into a two-dimensional array.
Figure 2B:
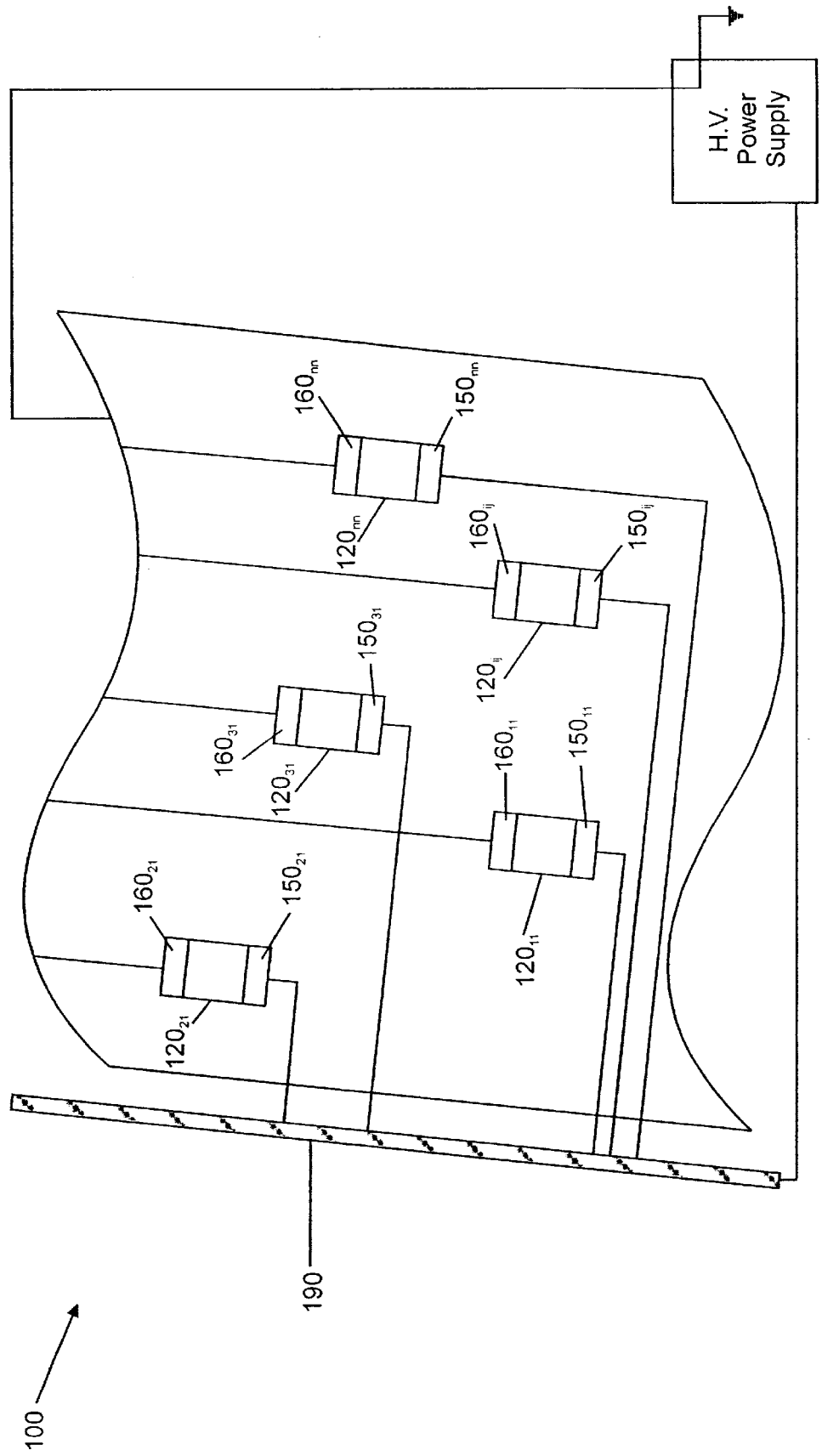

While a one-dimensional array has been discussed so far for simplicity, in practice the x-ray sources are arranged in a two-dimensional array, in a preferred embodiment of the present invention. FIGS. 2(a) and 2(b) illustrate a system 100 constructed according to a preferred embodiment of the present invention, in which the x-ray sources are disposed along a two-dimensional array. In the system 100, a plurality of miniature x-ray sources, $120_{11}$, $120_{12}$, ... $120_{ij}$, ..., $120_{nn}$, are positioned on a two-dimensional surface I 12, and arranged into a two-dimensional array. The elements of the two-dimensional array may be uniformly spaced, or variably spaced.

In the embodiment illustrated in FIG. 2(a), the two-dimensional array of x-ray sources $120_{ij}$ is rectilinear, and formed by connecting a plurality of linear, one-dimensional arrays $130_1$, ... $130_i$, ... $130_n$. Each linear array $130_i$ includes a plurality of x-ray sources, $120_{i1}$, $120_{i2}$, ..., $120_{ij}$, ... $120_{in}$, which are enclosed in a flexible metallic catheter or tube $114_i$. The x-ray sources $120_{ij}$ may be viewed as being arranged into rows and columns, i.e. each linear array $130_i$ may be viewed as a row or a column forming the rectilinear two-dimensional array. In one form of the invention, each linear array $130_i$ is moveable with respect to each other, for example via a mechanical assembly 195. Spacers $170_i$ may be used to maintain each linear array $130_i$ at desired spacings from adjacent linear arrays $130_{i-1}$ and $130_{i+1}$.

As illustrated in FIG. 2(b), the two-dimensional array is not limited to a rectilinear configuration, and the surface 112 can have any desired configuration. FIG. 2(b) illustrates a plurality of x-ray sources disposed on a flexible, curved surface 112. The configuration of the array may be tailored to the particular treatment being delivered, the geometry of the body region being treated, and the desired radiation dose pattern. In one embodiment of the invention, the two-dimensional surface may be a substantially flat, planar surface. In other embodiments, the surface may be a substantially concave, or a substantially convex surface. The surface may be substantially rigid. For example, the x-ray sources may be positioned on an inflexible sheet. Alternatively, the surface may be a substantially flexible, conformable surface. The surface may be substantially cylindrical, or substantially spherical. The surface may be defined by one or more axes. The axes may be straight axes, as in the case of the rectilinear array illustrated in FIG. 2(a), or may be curvilinear axes that define a non-rectilinear array. The x-ray sources in the two-dimensional array may be positioned in a radially symmetrical pattern, or in a hexagonally symmetrical pattern. The variety of possible configurations of the arrays eliminates the need for complex positioning systems for the x-ray sources.

Figure 3:
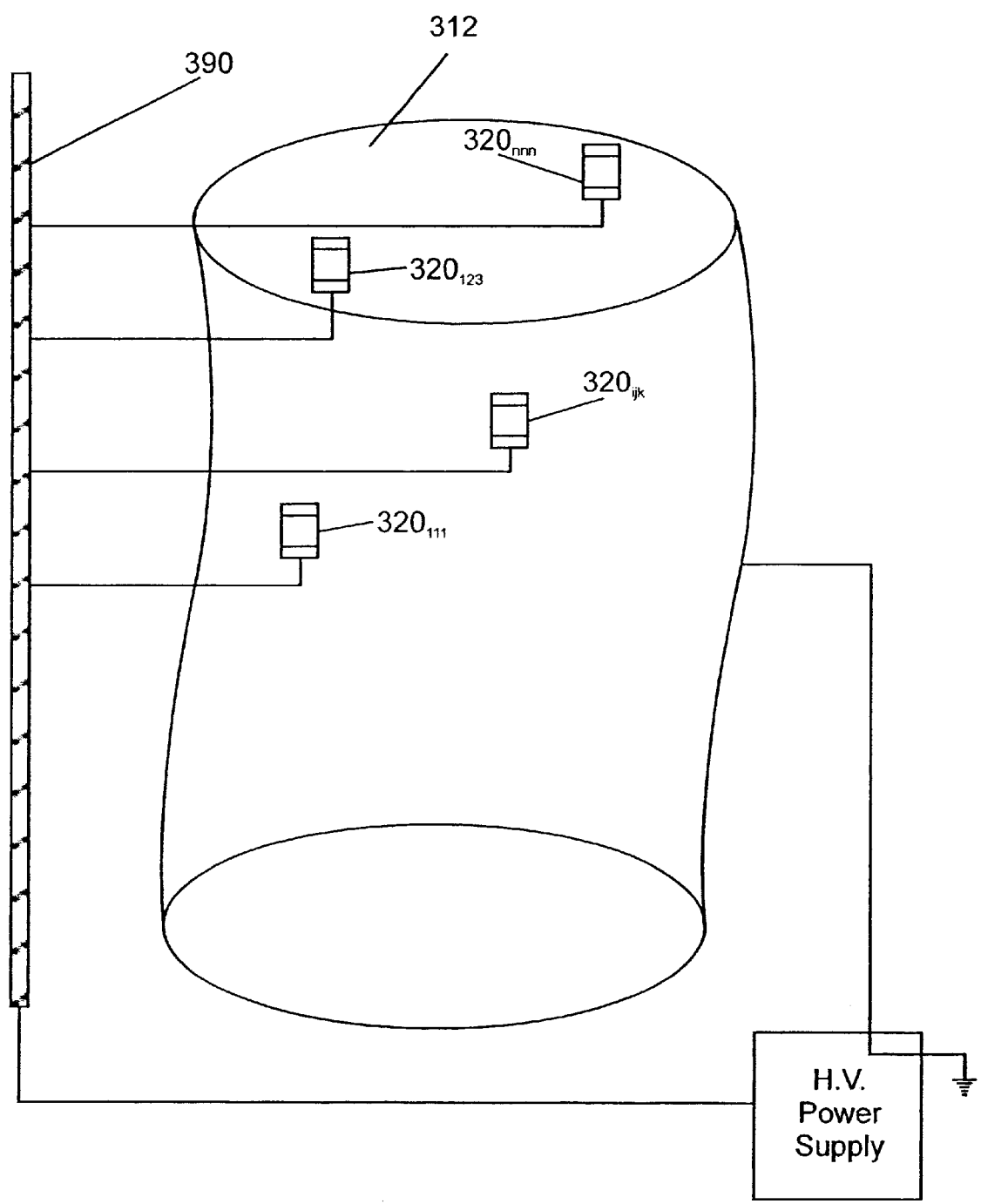
FIG. 3 illustrates an embodiment of the present invention in which a plurality of therapeutic radiation sources are arranged into a three-dimensional array.

FIG. 3 illustrates an embodiment of the present invention in which a plurality of therapeutic radiation sources $320_{ijk}$ are selectively and moveably positioned within a three-dimensional volume 312, and arranged into a three-dimensional array. Each therapeutic radiation source $320_{ijk}$ is disposed within the three-dimensional volume 312, and as elements of a three-dimensional array. By analogy to the case of one- and two-dimensional arrays, the three-dimensional array may have any desired configuration. In FIG. 3, the three-dimensional array is illustrated as having an irregular, curvilinear configuration. In other embodiments of the invention, the three-dimensional array may have a rectilinear configuration.

Figure 4:
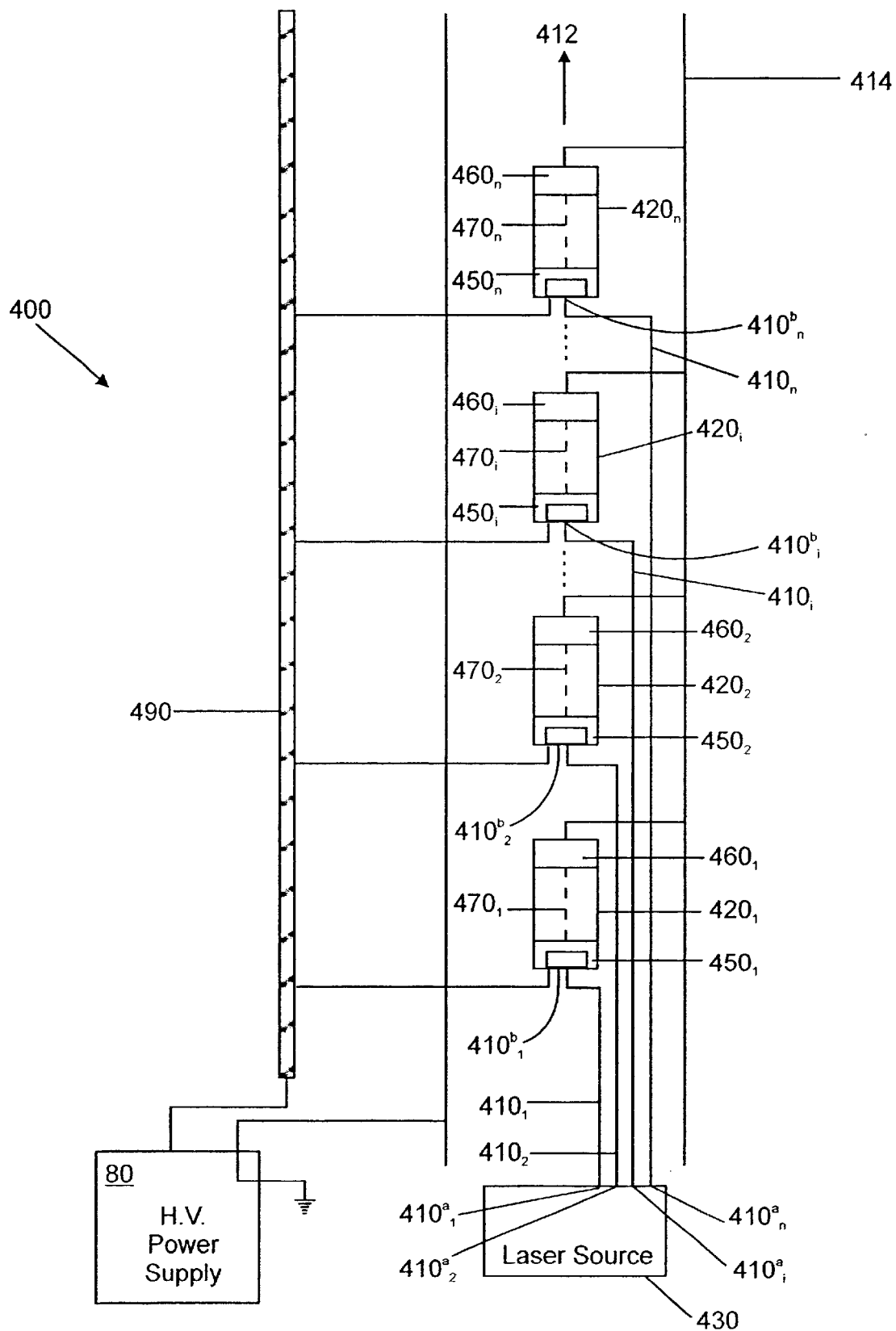
FIG. 4 illustrates a system for delivering therapeutic radiation, in which a plurality of optically activated x-ray sources, each coupled to the distal end of an associated fiber optic cable, are arranged along an axis in a one-dimensional array.

FIG. 4 illustrates one embodiment of a system 400 for delivering therapeutic radiation in accordance with the present invention, which includes a plurality of optically activated x-ray sources $420_i$. A one-dimensional configuration is illustrated for simplicity, however, two and three dimensional arrays of optically activated x-ray sources are also within the scope of this invention. In this embodiment, each of the plurality of x-ray sources $420_i$ is coupled to an associated fiber optic cable $410_i$. The system 400 thus includes a plurality of fiber optic cables $410_1$, $410_2$, ..., $410_i$, ..., $410_n$, and a corresponding plurality of x-ray sources $420_1$, $420_2$, ..., $420_i$, ..., $420_n$. In the illustrated embodiment, the plurality of n point-like x-ray sources $420_i$ are disposed along an axis 412 so as to form a one-dimensional array.

Each x-ray source $420_i$ in the illustrated embodiment comprises an electron source $450_i$, typically a cathode, and an associated target element $460_i$. Each electron source $450_i$ is optically activated. Each fiber optic cable $410_i$ has a proximal end $410_i^a$ and a distal end $410_i^b$. Each x-ray source $420_i$ is coupled to the distal end $410_i^b$ of its corresponding fiber optic cable $410_i$.

The system 400 further includes one or more light sources 430, which generate a beam of light directed to the proximal end of each fiber optic cable. The proximal end $410_i^a$ of each fiber optic cable $410_i$ is optical coupled to the one or more laser sources 430, and the distal end $410_i^b$ of each fiber optic cable 410 is disposed along the axis 412. In a preferred embodiment, the one or more light sources 430 are laser sources that generate substantially monochromatic and coherent beams of laser light, although in other embodiments of the invention, other sources of high intensity light, such as LEDs (light emitting diodes) may be used. The laser source 430 may be a Nd:YAG laser or a Nd:YVO$_4$ laser, by way of example. Other lasers known in the art may be used, including but not limited to diode lasers, molecular lasers, and solid state lasers. As well known, each fiber optic cable $410_i$ is adapted to transmit optical radiation that is incident on the proximal end $410_i^a$ of the fiber optic cable $410_i$ to the distal end $410_i^b$ of the cable, by total internal reflection.

The optically activated cathode $450_i$ is responsive to light that is transmitted to the distal end $410_i^b$ of the associated fiber optic cable $410_i$ and that is incident upon the cathode $450_i$, to emit electrons to generate an electron beam $470_i$ along a beam path. The cathode $450_i$ may be a laser-heated thermionic cathode which emits electrons when heated to a sufficient temperature, or a photocathode which emits electrons by the photoelectric effect in response to an incident light beam. The target element $460_i$, associated with the electron source $450_i$, is positioned in the electron beam path. The target element $460_i$ includes at least one x-ray emissive material for emitting x-rays, in response to incident accelerated electrons from the electron beam.

Figure 5:
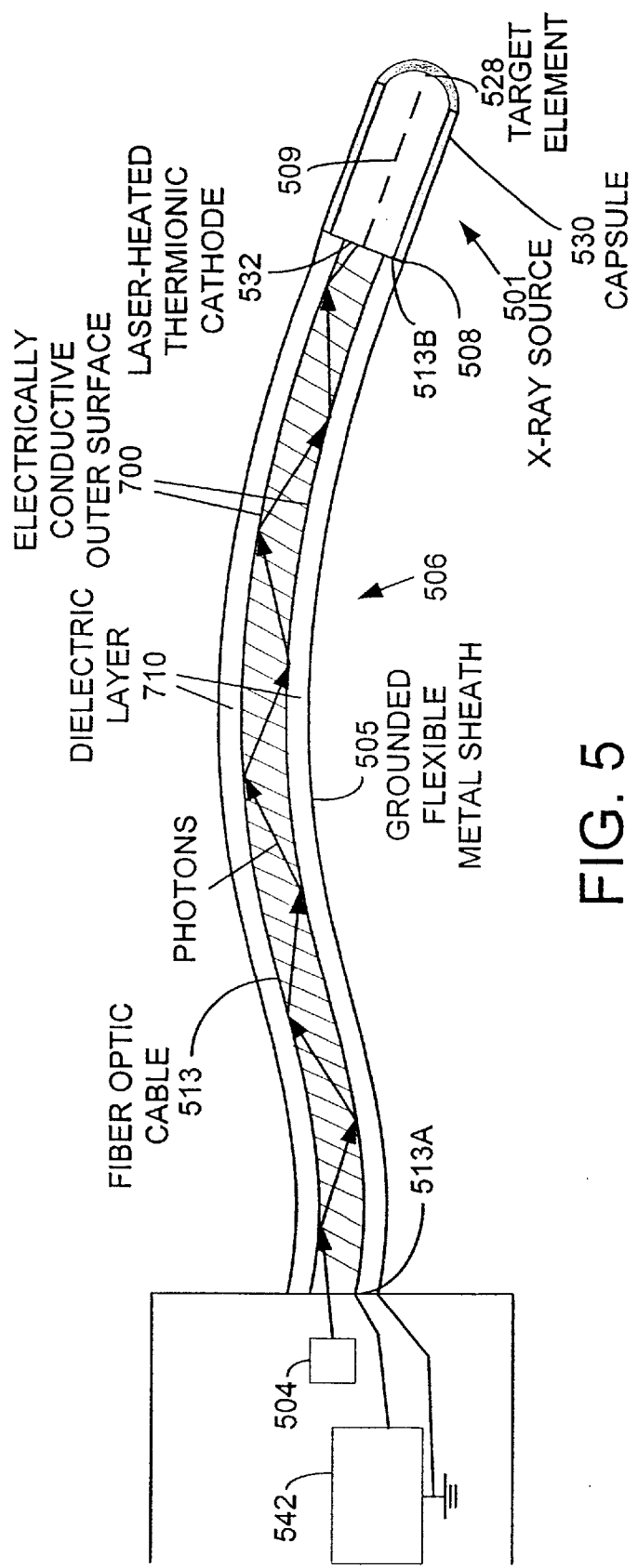
FIG. 5 illustrates in more detail a single component of the one- or multi-dimensional arrays that form a system constructed according to the present invention, namely a single x-ray source for delivering therapeutic radiation.

FIG. 5 illustrates in more detail a single component of the one- or multi-dimensional arrays discussed above, namely a single optically driven x-ray source and its associated fiber optic cable. In particular, FIG. 5 illustrates an individual x-ray source 501 having a laser-driven thermionic cathode, and an associated fiber optic cable 513. A miniature x-ray source having a laser-driven thermionic cathode is disclosed in the '561 application, and is incorporated herein by reference, as mentioned earlier. The x-ray source 501 includes an electron source 508, and a target element 528. The target element 528 includes at least one x-ray emissive material that emits x-rays, in response to accelerated electrons from the electron source 508. The x-ray source 501 is coupled to a corresponding optical delivery structure 513, preferably a flexible fiber optic cable. In the illustrated embodiment, the x-ray source 501 is coupled to the distal end of the fiber optic cable, and an electrically conductive sheath 505 encloses the fiber optic cable 513. The x-ray source 501 may include a shell or capsule 530 which encloses the electron source 508 and the target element 528. A high voltage power supply 542 provides an accelerating voltage between the electron source 508 and the target element 528.

The fiber optic cable 513 has a proximal end 513A, and a distal end 513B. In the illustrated embodiment, the optical delivery structure 513 is enclosed within a flexible, electrically conductive catheter 505, although a rigid probe may be used in other embodiments of the invention. The distal end 513B of the optical cable 513 is coupled to the x-ray source 501. In a preferred embodiment, the optical delivery structure 513 is a flexible fiber optic cable extending from the proximal end 513A to the distal end 513B. As well known in the art, the fiber optic cable 513 is adapted to transmit optical radiation that is incident on the proximal end 513A of the fiber optic cable 513 to the distal end 513B thereof, by total internal reflection.

In the illustrated embodiment, the flexible catheter 505 that encloses the flexible fiber optic cable 513 is a small-diameter, flexible metallic outer sheath. In a preferred embodiment, the fiber optic cable 513 includes an electrically conductive outer surface 700. For example, the outer surface of the fiber optic cable 513 may be made conductive by applying an electrically conductive coating. The electrically conductive outer surface 700 of the fiber optic cable 513 provides a connection to the electron source 508 from the high voltage power supply 542. In this embodiment, the capsule 530 that encloses the electron source 508 and the target element 528 also has an electrically conductive outer surface. Preferably, both the flexible metallic sheath 505 and the outer conductive surface of the radiation generator assembly 501 are set at ground potential, in order to reduce the shock hazard of the device. The flexible sheath 505 couples a ground return from the target element 528 to the high voltage power supply 542, thereby establishing a high voltage field between the electron source 508 and the target element 528. In an exemplary embodiment, the fiber optic cable 513 may have a diameter of about 200 microns, and the flexible metallic sheath 505 may have a diameter of about 1.4 mm, although other sizes maybe used. A layer 710 of dielectric material provides insulation between the outer surface of the fiber optic cable 513 and the inner surface of the metallic sheath 505.

The x-ray source 501, which can for example be about 0.5 to about 2 cm in length, extends from the distal end of the probe assembly 506 and includes a shell or capsule 530 which encloses the electron source 508 and the target element 528. According to one embodiment, the capsule 530 is rigid in nature and generally cylindrical in shape. In this embodiment, the cylindrical capsule 530, enclosing the other elements of the x-ray source 501, can be considered to provide a substantially rigid housing for the electron source 508 as well as for the target element 528. The capsule 530 defines a substantially evacuated interior region along a reference axis 509, between the electron source 508 at a proximal end of the capsule 530 and an x-ray transmissive window at a distal end of the capsule 530. The capsule 530 may be made of an x-ray transparent glass or ceramic material, by way of example. Preferably, the wall of the capsule 530 is an electrical insulator, while the external surface of the capsule 530 is electrically conductive. According to a preferred embodiment, the x-ray source 501 is hermetically sealed to the distal end of the probe assembly 506, and evacuated. According to another embodiment, the probe assembly 506 may be hollow, and the probe assembly 506 and the x-ray source 501 are evacuated.

In the embodiment illustrated in FIG. 5, the electron source 508 is a thermionic cathode 532 having an electron emissive surface facing the target element 528. As known in the art, electrons are emitted from the electron emissive surface of the thermionic cathode 532 into the surrounding vacuum, when the surface is heated to a sufficient temperature. The electrons are emitted with a Maxwellian distribution of velocities corresponding to the cathode temperature. In a preferred form, the thermionic cathode 532 is disc shaped. However, in other embodiments of the invention other cathode configurations may be used, for example spiral-shaped configurations, as disclosed in related U.S. application Ser. No. 09/884,229 (commonly owned by the assignee of the present invention and incorporated herein by reference). The cathode 532 may be held in place by swage of the end or by laser welding. The cathode 532 may be formed of a metallic material, including tungsten, thoriated tungsten, other tungsten alloys, and tantalum.

In one embodiment, the cathode 532 may be formed by depositing a layer of electron emissive material on a base material, so that an electron emissive surface is formed thereon. By way of example, the base material may be formed from one or more metallic materials, including but not limited to Group VI metals such as tungsten, and Group II metals such as barium. In one form, the layer of electron emissive material may be formed from materials including, but not limited to, aluminum tungstate and scandium tungstate. The thernionic cathode 532 may also be an oxide coated cathode, where a coating of the mixed oxides of barium and strontium, by way of example, may be applied to a metallic base, such as nickel or a nickel alloy.

The x-ray source 501 also includes means 542 for providing an accelerating voltage between the electron source 508 and the target element 528, typically a high voltage supply, as described in conjunction with FIG. 1.

The target element 528 is preferably spaced apart from and opposite the electron emissive surface of the thermionic cathode 532, and has at least one x-ray emissive material adapted to emit x-rays in response to incident accelerated electrons from the cathode 532. In one embodiment, the target element 528 is a small beryllium (Be) substrate, coated on the side exposed to the incident electron beam with a thin film or layer of a high-Z element, such as tungsten (W), uranium (U) or gold (Au). As the atomic number of the x-ray emissive element increases, the peak output in the spectral distribution curve of the emitted x-rays, and the characteristic spectral lines of the x-rays, shift to higher energies. The efficiency of x-ray generation is highly dependent on the acceleration voltage provided by the high voltage power supply 542, although independent of the electron beam current. By way of example, when the electrons are accelerated to 30 keV-, a 2.2 micron thick tungsten layer absorbs substantially all of the incident electrons, while transmitting approximately 95% of any 30 keV-, 88% of any 20 keV-, and 83% of any 10 keV-x-rays generated in that layer. In this embodiment, the beryllium substrate is 0.5 mm thick. With this configuration, 95% of the x-rays generated in directions normal to and toward the beryllium substrate, and having passed through the tungsten layer, are then transmitted through the beryllium substrate and outward at the distal end of the probe assembly 506. X-rays emitted from the target element 528 are directed through the x-ray transmissive window of the capsule 530 onto a desired region-to-be-treated.

In some forms of the target, the target element 528 may include a multiple layer film, where the differing layers may have different emission characteristics. By way of example, the first layer may have an emission peak at a relatively low electron energy, and the second, underlying layer may have an emission peak at a relatively high electron energy. With this form of the invention, a low energy electron beam may be used to generate x-rays in the first layer to achieve a first radiation characteristic, and high energy electrons may be used to penetrate through to the underlying layer to achieve a second radiation characteristic. As an example, a 0.5 mm wide electron beam is emitted at the cathode 532 and accelerated to 30 keV, with 0.1 eV transverse electron energies, and arrives at the target element 528, with a beam diameter of less than 1 nm at the target element 528. X-rays are generated in the target element 528 in accordance with pre-selected beam voltage, current, and target material composition. The x-rays thus generated pass through the beryllium substrate with minimized loss in energy. As an alternative to beryllium, the target substrate may be made of carbon or other suitable material which permits x-rays to pass with a minimum loss of energy. An optimal material for target substrate is carbon in its diamond form, since that material is an excellent heat conductor. Using these parameters, the resultant x-rays have sufficient energy to penetrate into soft tissues to a depth of a centimeter or more, the exact depth dependent upon the x-ray energy distribution.

The fiber optical cable 513 directs the beam of laser radiation, which has been transmitted therethrough, to impinge upon the electron emissive surface of the thermionic cathode 532. The beam of laser radiation must have a power level sufficient to heat at least a portion of the electron emissive surface to an electron emitting temperature so as to cause thermionic emission of electrons from the surface. It has been found that only a few watts of power is needed to generate over 100 $\mu$A of electron current, using a Nd:YAG laser coupled into a $SiO_2$ optical fiber having a diameter of 400 microns. In another example, an infrared diode laser was used to achieve about 100 $\mu$A of electron current with only 180 mW of power. The laser beam rapidly heats the surface of the cathode 532 to an electron emitting temperature, below the melting point of the metallic cathode 532. When the surface reaches an electron emitting temperature, electrons are thermionically emitted from the surface into the vacuum provided by the capsule 530. The high voltage field between the cathode 532 and the target element 528 accelerates these electrons, thereby forcing them to strike the surface of the target element 528 and emit x-rays.

Alternatively, the cathode 532 may be a photocathode, rather than a laser-driven thermionic cathode. The photocathode has a photoemissive surface coated with a semi-transparent photoemissive substance, such as Ag—O—Cs. In this embodiment, the laser beam shining down the fiber optic cable 513 activates the transmissive photocathode, which generates free electrons by the photoelectric effect. The high voltage field between the cathode 532 and the target element 528 accelerates these electrons, thereby forcing them to strike the surface of target element 528 and produce x-rays.

A photocathode must have a sufficient quantum efficiency, where quantum efficiency relates to the number of electrons generated per incident light quantum. The degree of efficiency must be balanced to the intensity of available incident light. In order to generate, for example, 20 $\mu$A of current from a Ag—O—Cs photocathode with a laser emitting light at a wavelength of 0.8 $\mu$m, the 0.4% quantum efficiency of this photocathode for this wavelength requires that the laser emits 7.5 mW optical power. Such diode lasers are readily commercially available. According to this embodiment, the photoemissive surface which forms the photocathode can, in fact, be quite small. For example, for a current density at the photocathode of 1 A per $cm^2$, the photoemitter's diameter need only be approximately 50 $\mu$m.

In the above embodiments, the probe assembly 506, along with the x-ray source 501, can be coated with a biocompatible outer layer, such as titanium nitride on a sublayer of nickel. For additional biocompatibility, a sheath of, for example, polyurethane can be fitted over the catheter 505.

In operation, the one- or multi-dimensional array of miniature x-ray sources may be used for a wide variety of treatment purposes. A one-dimensional array of x-ray sources may be used in conjunction with the cardiovascular treatment of blood vessels, by way of example. A linear array of x-ray sources may be inserted into a blood vessel, for example in order to treat lesions that are located along the interior wall of a blood vessel, such as a coronary artery. In this case, each x-ray source may be threaded down the vessel or artery, by means of the small-diameter, flexible tubes. Alternatively, a two-dimensional array of point x-ray sources may be used in oncology for treatment of cancerous tumors. A two-dimensional array of x-ray sources may be positioned upon a two-dimensional surface that conforms to the contours of a treatment region within a patient's body. Typically, the tumors are found at random and irregular locations within the treatment region. The treatment region may be a bodily organ affected with cancer, such as an esophagus, a bladder, a prostate, a lung, a bone, or other bodily part or organ. The x-ray sources may be variably spaced along the surface.

Once the individual x-ray sources are positioned at the desired locations, the laser source may be activated so that laser light is transmitted down one or more selected fiber optic cables. As explained earlier, this activates the associated electron source, which generates an electron beam. The power supply may then be activated, so that a high voltage field between the electron source and the target element accelerates the electrons, thereby forcing them to strike the surface of the target element and produce x-rays.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A system for delivering therapeutic radiation to a treatment region, the system comprising:
   A. a plurality of therapeutic radiation sources selectively and moveably disposed along an array,
   wherein each therapeutic radiation source comprises:
      a. an electron source for generating electrons, and
      b. a target element associated with said electron source, said target element including at least one radiation emissive material adapted to emit therapeutic radiation in response to incident accelerated electrons from said electron source; and
   B. means for providing an accelerating voltage between each electron source and each associated target element so as to establish an accelerating electric field which acts to accelerate electrons generated by said electron source toward said associated target element.

2. A system according to claim 1, wherein said therapeutic radiation comprises x-rays, and wherein said radiation emissive material comprises x-ray emissive material.

3. A system according to claim 1, wherein said array comprises a two-dimensional array.

4. A system according to claim 1, wherein said array comprises at least one of a one-dimensional array and a three-dimensional array.

5. A system according to claim 1, wherein said plurality of therapeutic radiation sources are disposed along one or more axes.

6. A system according to claim 5, wherein said one or more axes includes at least one of a substantially straight axis, a substantially rigid axis, a substantially curvilinear axis, a substantially flexible axis, and a deformable axis.

7. A system according to claim 1, further comprising:
A. at least one outer tubular member for enclosing said plurality of therapeutic radiation sources, said tubular member being adapted for insertion into an anatomical region; and
B. control means for activating at least one of said plurality of therapeutic radiation sources when said tubular member is inserted within said anatomical region so as to enable delivery of therapeutic radiation onto at least a portion of said anatomical region.

8. A system according to claim 7, further including a mechanical assembly for inserting said tubular member into said anatomical region, and for withdrawing said tubular member from said anatomical region.

9. A system according to claim 7, wherein each of said plurality of therapeutic radiation sources are individually and selectively moveable within said outer tubular member and with respect to each other.

10. A system according to claim 1, wherein the elements of said array are uniformly spaced.

11. A system according to claim 1, wherein the elements of said array are variably spaced.

12. A system according to claim 1, wherein electrons incident on each target element from each electron source are accelerated by said accelerating electric field to energies in the approximate range of 10 kV to 90 kV.

13. A system according to claim 1, further comprising selectively operable control means including means for selectively controlling the magnitude of said acceleration voltage.

14. A system according to claim 13, wherein the magnitude of said acceleration voltage is independently controllable for two or more of said plurality of therapeutic radiation sources.

15. A system according to claim 1, wherein each electron source generates an electron beam along a beam path, and wherein each associated target element is positioned in said beam path.

16. A system according to claim 15, wherein said electron beam is characterized by a current in the approximate range of 1 nA to 1 mA.

17. A system according to claim 16, further comprising selectively operable control means including means for selectively controlling the amplitude of said beam current.

18. A system according to claim 17, wherein the amplitude of said beam current is independently controllable for two or more of said therapeutic radiation sources.

19. A system according to claim 1,
wherein said electron source comprises a thermionic cathode.

20. A system according to claim 19, wherein said thermionic cathode is an optically driven thermionic cathode having an electron emissive surface adapted to emit electrons when heated to a sufficient temperature by a beam of optical radiation.

21. A system according to claim 1, wherein the electron source in at least one of said plurality of therapeutic radiation sources includes a photocathode having a photoemissive surface, said photocathode being responsive to optical radiation incident thereon to emit electrons from said photoemissive surface.

22. A system according to claim 1, wherein at least one of said plurality of therapeutic radiation sources comprises a substantially rigid capsule enclosing said electron source and said target element and defining a substantially evacuated interior region, said capsule comprising a radiation transmissive window wherein therapeutic radiation emitted from said target element is directed through said radiation transmissive window.

23. A system according to claim 1, wherein said means for providing an accelerating voltage comprises:
a) a high voltage power supply; and
b) at least one electrical conductor for electrically coupling said high voltage power supply to one or more of said plurality of therapeutic radiation sources.

24. A system for delivering therapeutic radiation, the system comprising:
A. a plurality of therapeutic radiation sources selectively and moveably disposed on a two-dimensional surface and arranged into a two-dimensional array;
wherein each therapeutic radiation source comprises:
a. an electron source for generating electrons; and
b. a target element associated with said electron source, said target element including at least one radiation emissive material for emitting therapeutic radiation in response to incident accelerated electrons from said electron source; and
B. means for providing an accelerating voltage between each electron source and each associated target element so as to establish an accelerating electric field which acts to accelerate electrons emitted from said electron source toward said associated target element.

25. A system according to claim 24, wherein the magnitude of said acceleration voltage is independently controllable for two or more of said plurality of therapeutic radiation sources.

26. A system according to claim 24, wherein each electron source generates an electron beam along a beam path;
wherein each associated target element is positioned in said beam path; and
wherein said electron beam is characterized by a current in the approximate range of 1 nA to 1 mA.

27. A system according to claim 24, wherein the amplitude of said beam current is independently controllable for two or more of said therapeutic radiation sources.

28. A system according to claim 24, wherein the therapeutic radiation sources in said two-dimensional array are disposed in at least one of a radially symmetrical pattern, and a hexagonal pattern.

29. A system according to claim 24, wherein said two-dimensional surface comprises at least one of a substantially rigid surface, a substantially flexible surface, and a substantially planar surface.

30. A system according to claim 24, wherein said two-dimensional surface comprises at least one of a substantially concave surface, a substantially convex surface, a substantially spherical surface, and a substantially cylindrical surface.

31. A system for delivering therapeutic radiation, the system comprising:
A. a plurality of therapeutic radiation sources selectively and moveably disposed within a three-dimensional volume and arranged into a three-dimensional array, each therapeutic radiation source comprising:
   a. an electron source for generating electrons, and
   b. a target element associated with said electron source, said target element including at least one radiation emissive material for emitting therapeutic radiation in response to incident accelerated electrons from said electron source; and
B. means for providing an accelerating voltage between each electron source and each associated target element so as to establish an accelerating electric field which acts to accelerate electrons emitted from said electron source toward said associated target element.

32. A system for delivering therapeutic radiation to a treatment region, the system comprising:
A. a plurality of optical delivery structures, each optical delivery structure having a proximal end and a distal end, each optical delivery structure being adapted for transmitting light incident on said proximal end to said distal end; and
B. a corresponding plurality of therapeutic radiation sources selectively and moveably disposed along an axis so as to form a one-dimensional array, each therapeutic radiation source being coupled to the distal end of an associated optical delivery structure;
wherein each therapeutic radiation source comprises:
   a. an electron source, responsive to light transmitted to said distal end of said associated optical delivery structure, for generating electrons, and
   b. a target element associated with said electron source, said target element including at least one radiation emissive material for emitting therapeutic radiation in response to incident accelerated electrons from said electron source;
C. one or more optical sources, including means for generating for each of said plurality of therapeutic radiation sources a beam of optical radiation directed to the proximal end of the associated optical delivery structure; and
D. means for providing an accelerating voltage between each electron source and each associated target element so as to establish an accelerating electric field which acts to accelerate electrons generated by said electron source toward said associated target element.

33. A system according to claim 32, wherein said plurality of optical delivery structures comprises a fiber optic cable.

34. A system according to claim 32, wherein the proximal end of each of said plurality of optical delivery structures is optically coupled to one of said one or more light sources, and the distal end of each of said plurality of optical delivery structures is disposed along said axis.

35. A system according to claim 32, wherein said at least one optical source comprises a laser source, and wherein said beam of transmitted light is substantially monochromatic and coherent.

36. A system according to claim 32, wherein said laser source is selected from the group consisting of a diode laser, a molecular laser and a solid state laser.

37. A system according to claim 32, wherein at least one of said plurality of optical delivery structures is enclosed within an electrically conductive, flexible, outer sheath.

38. A system for delivering therapeutic radiation, the system comprising:
A. a plurality of fiber optic cables, each fiber optic cable having a proximal end and a distal end, each fiber optic cable being adapted for transmitting light incident on said proximal end to said distal end; and
B. a corresponding plurality of therapeutic radiation sources selectively and movably disposed along an axis so as to form a one-dimensional array, each therapeutic radiation source being coupled to the distal end of an associated fiber optic cable;
wherein each therapeutic radiation source comprises:
   a. an electron source, responsive to light transmitted to said distal end of said associated fiber optic cable, for emitting electrons to generate an electron beam along a beam path, wherein said electron source comprises a thermionic cathode having an electron emissive surface; and
   b. a target element associated with said electron source and positioned in said beam path, said target element including means for emitting therapeutic radiation in response to incident accelerated electrons from said electron beam;
C. one or more light sources, including means for generating for each of said plurality of therapeutic radiation sources a beam of light directed to the proximal end of the associated fiber optic cable; and
D. means for providing an accelerating voltage between each electron source and each associated target element so as to establish an accelerating electric field which acts to accelerate electrons emitted from each electron source toward the associated target element;
wherein at least one fiber optic cable is adapted for directing a beam of transmitted light to impinge upon an electron emissive surface of a thermionic cathode in the therapeutic radiation source associated with said at least one fiber optic cable; and
wherein said beam of transmitted light has a power level sufficient to heat at least a portion of said surface to an electron emitting temperature so as to cause thermionic emission of electrons from said surface.

39. A system for delivering therapeutic radiation, the system comprising:
A. a plurality of fiber optic cables, each fiber optic cable having a proximal end and a distal end, each fiber optic cable being adapted for transmitting light incident on said proximal end to said distal end;
B. a corresponding plurality of therapeutic radiation sources selectively and moveably positioned on a two-dimensional surface and arranged into a two-dimensional array, each therapeutic radiation source being coupled to the distal end of an associated fiber optic cable;
wherein each therapeutic radiation source comprises:
   a. an electron source, responsive to light transmitted to said distal end of said associated fiber optic cable, for emitting electrons to generate an electron beam along a beam path, and
   b. a target element associated with said electron source and positioned in said beam path, said target element including at least one radiation emissive material for emitting therapeutic radiation in response to incident accelerated electrons from said electron beam;
C. one or more light sources, including means for generating for each of said plurality of therapeutic radiation sources a beam of light directed to the proximal end of the associated fiber optic cable; and D. means for providing an accelerating voltage between each electron source and each associated target element so as to establish an accelerating electric field which acts to accelerate electrons emitted from said electron source toward said associated target element;

wherein the proximal end of each of said plurality of fiber optic cables is optically coupled to one of said one or more light sources, and the distal end of each of said plurality of fiber optic cables is disposed on said two-dimensional surface and along said two-dimensional array.

40. A system for delivering therapeutic radiation, the system comprising:

A. a plurality of fiber optic cables, each fiber optic cable having a proximal end and a distal end, each fiber optic cable being adapted for transmitting light incident on said proximal end to said distal end;

B. a corresponding plurality of therapeutic radiation sources selectively and moveably positioned within a three-dimensional volume and arranged into a three-dimensional array, each therapeutic radiation source being coupled to the distal end of an associated fiber optic cable;

wherein each therapeutic radiation source comprises:

a. an electron source, responsive to light transmitted to said distal end of said associated fiber optic cable, for emitting electrons to generate an electron beam along a beam path, and b. a target element associated with said electron source and positioned in said beam path, said target element including at least one radiation emissive material for emitting therapeutic radiation in response to incident accelerated electrons from said electron beam;

C. one or more light sources, including means for generating for each of said plurality of therapeutic radiation sources a beam of light directed to the proximal end of the associated fiber optic cable; and D. means for providing an accelerating voltage between each electron source and each associated target element so as to establish an accelerating electric field which acts to accelerate electrons emitted from said electron source toward said associated target element;

wherein the proximal end of each of said plurality of fiber optic cables is optically coupled to one of said one or more light sources, and the distal end of each of said plurality of fiber optic cables is disposed within said three-dimensional volume and along said three-dimensional array.

\* \* \* \* \*